United States Patent [19]

Havera et al.

[11] 4,304,913
[45] Dec. 8, 1981

[54] TRANS-2-SUBSTITUTED-AMIDO-HEXAHYDROBENZO [a]QUINOLIZINES

[75] Inventors: Herbert J. Havera, Edwardsburg, Mich.; Wallace G. Strycker, Goshen, Ind.

[73] Assignee: Miles Laboratories, Inc., Elkhart, Ind.

[21] Appl. No.: 193,150

[22] Filed: Oct. 2, 1980

Related U.S. Application Data

[63] Continuation-in-part of Ser. No. 106,495, Dec. 26, 1979, abandoned, which is a continuation-in-part of Ser. No. 962,286, Nov. 20, 1978, abandoned.

[51] Int. Cl.$^3$ ............................................. C07D 455/06
[52] U.S. Cl. ..................... 546/95; 424/258; 546/65
[58] Field of Search ........................ 546/95; 424/258

[56] References Cited

U.S. PATENT DOCUMENTS

| | | | |
|---|---|---|---|
| 3,634,431 | 1/1972 | Van Dyke | 546/95 |
| 3,635,986 | 1/1972 | Van Dyke | 546/95 |
| 4,076,820 | 2/1978 | Archibald et al. | 546/95 X |

OTHER PUBLICATIONS

*Chemical Abstracts*, 89: 43086n (1978)[Hadley, M., et al., German Ols 2,748,260, 5/11/78].

*Primary Examiner*—Richard A. Schwartz
*Attorney, Agent, or Firm*—Jerome L. Jeffers

[57] ABSTRACT

Disclosed are trans-2-substituted-amido-hexahydrobenzo[a]quinolizines represented by the formula:

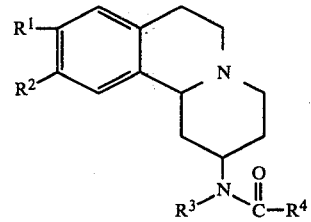

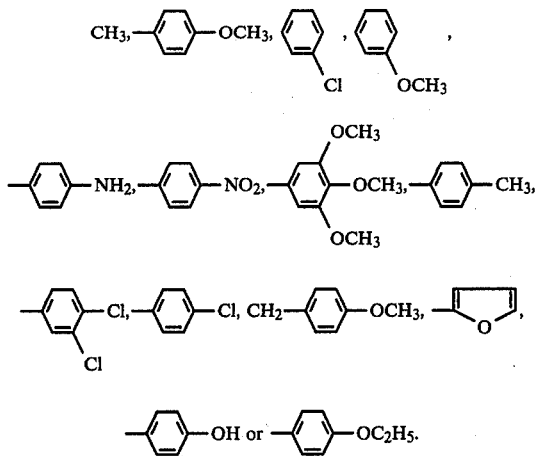

In the above formula, $R^1$ and $R^2$ are independently —H or —OCH$_3$ or when taken together are —O—CH$_2$—O— $R^3$ is —H or —CH$_3$ and $R^4$ is These compounds, and their pharmacologically acceptable, non-toxic, acid addition salts are useful as antihypertensive agents.

7 Claims, No Drawings

TRANS-2-SUBSTITUTED-AMIDO-HEXAHYDROBENZO [A]QUINOLIZINES

BACKGROUND OF THE INVENTION

This application is a continuation-in-part of application Ser. No. 106,495 filed Dec. 26, 1979, now abandoned, which is in turn a continuation-in-part of application Ser. No. 962,286 filed Nov. 20, 1978, now abandoned.

U.S. Pat. No. 3,635,986 (issued Jan. 18, 1972) discloses 2-substituted amino-hexahydrobenzo[a]quinolizines of the formula:

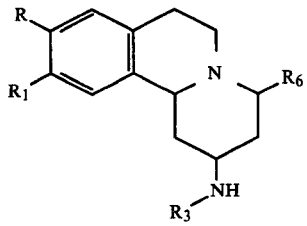

where R is H, OH or O-(lower) alkyl, $R_1$ is H, OH or O-(lower) alkyl, $R_6$ can be H and $R_3$ is defined as H, lower alkyl, cycloslkyl of between 3 and 7 carbon atoms alkyl, cycloalkyl of between 3 and 7 carbon atoms, phenyl, substituted phenyl, diphenyl, phenyl (lower) alkyl and substituted phenyl (lower) alkyl.

Compounds of the formula:

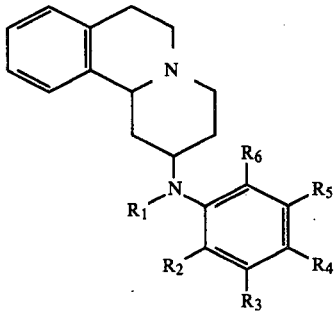

wherein $R_1$ is hydrogen or an alkanoyl group of 2 to 4 carbon atoms and $R_2$–$R_6$ are hydrogen, hydroxy or methyl are disclosed in U.S. Pat. No. 3,995,041 issued Nov. 30, 1976.

Acylated and alkylated derivatives of 2-amino-hexahydrobenzo[a]quinolizines are disclosed in U.S. Pat. No. 3,634,431 issued Jan. 11, 1972. These compounds have the formula:

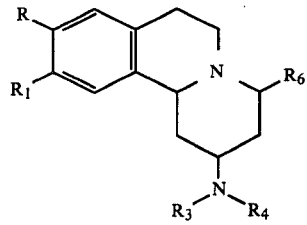

wherein R and $R_1$ are H, OH or lower alkoxy; $R_3$ is H, (lower) alkyl, cycloalkyl, phenyl, substituted phenyl, diphenyl, phenyl (lower) alkyl and substituted phenyl (lower) alkyl, $R_4$ can be

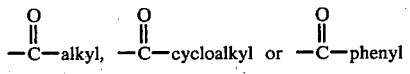

and $R_6$ can be H. This patent, in its Example 17, discloses the preparation of N-(1,3,4,6,7,11b-hexahydro-2H-benzo[a]quinolizine-2-yl)propionamide. These compounds are described as being useful as anti-hypertensive agents.

The compounds of the present invention are structurally similar to those disclosed in the prior art. The statement in the '431 patent that compounds of this general type have anti-hypertensive activity should not be taken as indicating that each and every species within the broad genus disclosed therein possesses such activity. This is the case because it has been determined that a substantial number of compounds falling within the scope of this generic formula do not possess anti-hypertensive activity. The compounds of the present invention all exhibit utility as anti-hypertensive agents. In addition, certain of the compounds disclosed herein, in contrast to prior art compounds of similar chemical structure, exhibit the ability to lower blood pressure without producing tachycardia.

Compounds lowering blood pressure by producing peripheral vasodilation, such as hydralazine, have found limited use in the treatment of arterial hypertension mainly because their blood pressure effect is accompanied by reflex cardiac stimulation (D. M. Aviado and H. Salem, in New Anti-hypertensive Drugs, A. Scriabine and C. S. Sweet, eds. Spectrum Publications, New York, 1975, p.527). Benzoquinolizine derivatives have been reported to decrease blood pressure by this mechanism (J. W. Van Dyke et al, J. Med. Chem. 15:91, 1972). Some of the present compounds elicit this effect without producing concomitant cardiac stimulation, as evidenced by their lack of effect on heart rate.

SUMMARY OF THE INVENTION

The present invention involves trans-2-substituted-amino-hexahydrobenzo[a]quinolizines represented by the formula:

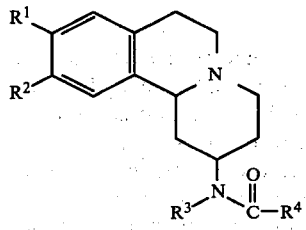

In the above formula $R^1$ and $R^2$ are independently —H or —OCH$_3$ or when taken together are

$R^3$ is —H or —CH$_3$ and $R^4$ is

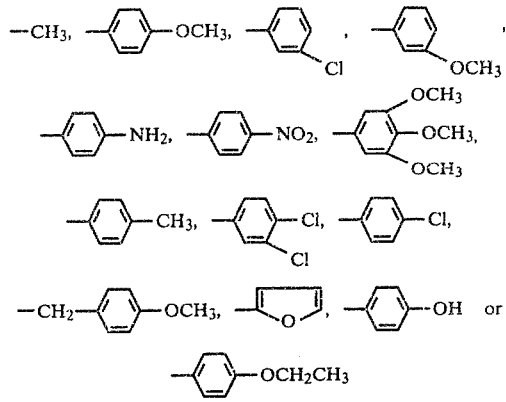

These compounds, and their pharmacologically acceptable, non-toxic, acid addition salts are useful as anti-hypertensive agents.

DETAILED DESCRIPTION AND PREFERRED EMBODIMENTS

The compounds of the present invention are conveniently prepared as follows:

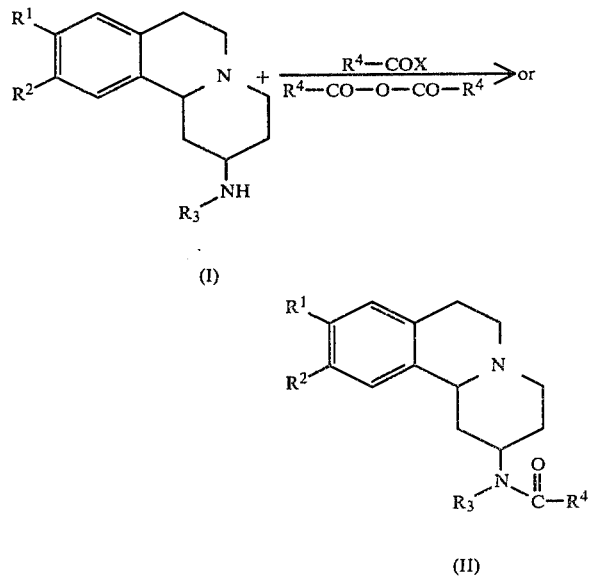

The above amine reactant (I) is subjected to an acylation with an acyl halide or anhydride having the desired $R^4$ radical to form the desired product (II). Although the operating conditions of this step are not critical, it is normally performed by stirring in the cold for about one hour. Warming on a steam bath or reflux conditions may be desirable under some circumstances. A base is normally employed to take up the acid formed in the reaction so that the free base of (II) is formed.

Amine (I) can be prepared by the following reaction sequence:

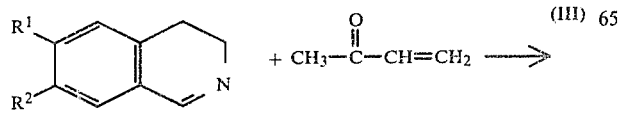

In the above reaction sequence, the isoquinoline (III) is reacted with 2-butene-3-one to form 2-oxo-1,3,4,6,7,11b-hexahydro-2H-benzo[a]quinolizine (IV). This synthesis is further described by Denes Beke and Csabe Szantay in Chem. Ber., 95, 2132–2136 (1962). The product of this reaction (IV) is reacted with an amine in a suitable solvent to form a Schiff base. The solvent used is not critical and may be dry toluene, benzene and xylene. The reaction mixture is advantageously maintained under reflux in the presence of a catalyst. The reaction time is not critical and is dependent upon the required amount of water being collected and may be between about one and twelve or more hours. The catalyst may be an acid actalyst and is preferably an organic acid catalyst such as p-toluenesulfonic acid. The Schiff base that is formed is then reduced to form the amine (I). This reaction is carried out in a suitable solvent such as methanol, ethanol or 2-propanol. To form the trans isomers (which are the subject matter of this invention), the reduction is beneficially carried out using $NaBH_4$.

Compound II were $R^4$ is 4-aminobenzo is prepared as described above except that the 2-(4-nitrobenzoamide) compound is first prepared and then reduced to amine.

The method of practicing the present invention is further illustrated by the following examples in which all temperatures are in degrees centigrade.

EXAMPLE 1

1,3,4,6,7,11b-Hexahydro-2-(N-methyl-N-propanoylamino)-2-H-benzo[a]quinolizine hydrochloride (TR-3413)

A solution of 1,3,4,6,7,11b-hexahydro-2-(N-methylamino)-2H-benzo[a]quinolizine (ca 8 g-crude) in 150 ml of benzene and 7 g of propionic anhydride was refluxed for 3 hours and concentrated in vacuo. The concentrate was converted to the HCl salt by addition of hydrogen chloride in 2-propanol and this solution also concentrated in vacuo. The oil was crystallized from acetone and recrystallized from 2-propanol-ether to yield 4.8 g of the desired product which was in the from of hygroscopic crystals, m.p. (decomposed at 190°–2°). This compound conforms to Formula II where $R_1$ and $R_2$ are H, $R_3$ is $CH_3$ and $R_4$ is $-CH_2CH_3$.

Anal. Calcd for $C_{17}H_{24}N_2O \cdot HCl$: C, 66.10; H, 8.16; N, 9.07; Found: C, 65.53; H, 8.25; N, 8.86.

EXAMPLE II

2-(N-Acetylamino)-1,3,4,6,7,11b-hexahydro-2H-benzo[a]quinolozine hydrochloride (TR-3697)

A solution of 2-amino-1,3,4,6,7,11b-hexahydro-2H-benzo[a]quinolizine (4.5 g) in 8 ml of concentrated HCl and 150 ml of water was reacted with 6 ml of acetic anhydride to which a solution of 25 g of NaOAc in 150 ml of water was added. The mixture was stirred for 2 hours, made strongly basic with 20% NaOH and extracted with chloroform. The chloroform extracts were dried over MgSO$_4$ and concentrated in vacuo to leave the free base as an oil. The free base was converted to the HCl salt with hydrogen chloride in a mixture of 2-propanol and ethyl acetate. The salt was isolated by evaporation of the solvent, and was recrystallized from 2-propanol-ethyl acetate and then from 2-propanol to yield 2.3 g of the desired product, m.p. (decomposed at 268°–70°). This compound conforms to Formula II where $R^1$ and $R^2$ are H, $R^3$ is H and $R^4$ is —CH$_3$.

Anal. Calcd for $C_{15}H_{20}N_2O$·HCl: C, 64.16; H, 7.54; N, 9.98; Found: C, 64.04; H, 7.26; N, 9.92.

EXAMPLE III

2-(N-Acetylamino)-1,3,4,6,7,11b-hexahydro-9,10-dimethoxy-2H-benzo[a]quinolizine hydrochloride (TR-3804)

A solution of 2-amino-1,3,4,6,7,11b-hexahydro-9,10-dimethoxy-2H-benzo[a]quinolizine (5 g) in 100 ml of 1:1 aqueous acetic acid was cooled to 5° and 2 g of acetic anhydride was added. The mixture was stirred at room temperature for 1 hour and concentrated in vacuo. The concentrate was dissolved in CHCl$_3$, washed with dilute NaOH, dried over MgSO$_4$ and concentrated in vacuo to leave an oil. The oil was chromatographed over silica gel using benzene-methanol (6:1) as eluant. The major fraction (4.5 g) was converted to the HCl salt with hydrogen chloride in a mixture of 2-propanol and ethyl acetate, isolated by removal of the solvent and recrystallized from 2-propanol-ethyl acetate to yield 3.9 g of the desired product, m.p. (decomposed at 240.0–240.4). This compound corresponds with Formula II where $R_1$ and $R_2$ are —OCH$_3$, $R_3$ is —H and $R_4$ is —CH$_3$.

Anal. Calcd for $C_{17}H_{24}N_2O_3$·HCl: C, 59.91; H, 7.39; N, 8.22; Found: C, 59.70; N, 7.32; N, 7.97.

EXAMPLE IV

2-Cyclopropylcarboxylamine-1,3,4,6,7,11b-hexahydro-9,10-dimethoxy-2H-benzo[a]-quinolizine hydrochloride (TR-3805)

A solution of 2-amino-1,3,4,6,7,11b-hexahydro-9,10-dimethoxy-2H-benzo[a]quinolizine (5 g, 0.019 mole) in 100 ml of benzene and 25 ml of 20% NaOH was cooled in an ice water bath and a solution of cyclopropylcarboxylic acid chloride (2.1 g) in 10 ml of benzene was added dropwise with stirring. The mixture was stirred in the cold for 30 minutes and at room temperature for 1 hour. The solid was collected and the benzene layer was separated and concentrated in vacuo. The combined solid and concentrate were recrystallized from benzene-petroleum ether to yield 3 g of the desired product, m.p. 195°–7°.

Anal. Calcd for $C_{19}H_{26}N_2O_3$: C, 69.07; H, 7.93; N, 8.48; Found: C, 68.75; H, 7.79; N, 8.38.

The free base (3 g) was chromatographed over silica gel using benzene-methanol (6:1) as the eluant. The major fraction (2.5 g) was converted to the HCl salt with hydrogen chloride in a 2-propanol-ether mixture. The salt was isolated by evaporation of the solvent and recrystallized from a mixture of 2-propanol, methanol and ether and again from absolute ethanol-ether to yield 2.2 g of the desired product, m.p. (decomposed at 260°–1°). This compound conforms to Formula II where $R^1$ and $R^2$ are —OCH$_3$, $R^3$ is H and $R^4$ is

Anal. Calcd for $C_{19}H_{26}N_2O_3$·HCl: C, 62.20; H, 7.42; N, 7.64; Found: C, 61.96; H, 7.39; N, 7.52

EXAMPLE V

2-Benzoylamino-1,3,4,6,7,11b-hexahydro-9,10-dimethoxy-2H-benzo[a]quinolizine hydrochloride (TR-3807)

A mixture of 2-amino-1,3,4,6,7,11b-hexahydro-9,10-dimethoxy-2H-benzo[a]quinolizine (5 g, 0.019 mole), 150 ml of benzene and 25 ml of 20% NaOH was cooled in an ice bath, and a solution of benzoyl chloride (2.7 g, 0.019 mole) in 10 ml of benzene was added dropwise with stirring. The mixture was stirred in the cold for 30 minutes and at room temperature for 1 hour. The solid was collected, dissolved in chloroform, washed with water, dried over MgSO$_4$ and concentrated in vacuo to leave a solid residue. The solid was crystallized from acetone-petroleum ether and chromatographed over silica gel using benzene-MeOH (9:1) as the eluant. The major fraction (3.9 g) was converted to the HCl salt with hydrogen chloride in 2-propanol, and concentrated in vacuo to isolate the salt. The salt was crystallized from methanol-ether and again from absolute ethanol-ether to yield 3.0 g of the desired product, m.p. (decomposed at 250°–1°). This compound conforms with Formula II where $R^1$ and $R^2$ are OCH$_3$, $R^3$ is H and $R^4$ is phenyl.

Anal. Calcd for $C_{22}H_{26}N_2O_3$·HCl: C, 65.59; H, 6.75; N, 6.95; Found: C, 65.37; H, 6.72; N, 6.84.

EXAMPLE VI

1,3,4,6,7,11b-Hexahydro-9,10-dimethoxy-2-propanoylamino-2H-benzo[a]quinolizine hydrochloride (TR-3813)

To a solution of 2-amino-1,3,4,6,7,11b-hexahydro-9,10-dimethoxy-2H-benzo[a]quinolizine (5 g, 0.019 mole) in 100 ml of benzene was added 2.6 g of propionic anhydride. The solution was warmed on a steam bath for 1 hour and then diluted with petroleum ether to precipitate a solid which was collected and chromatographed over silica gel using benzene-methanol (9:1) as eluant. The major fraction (4.5 g) was converted to the HCl salt with hydrogen chloride in 2-propanol and concentrated to an oil in vacuo. The oil was crystallized from methanol-ether and recrystallized from 2-propanol-ether to yield 2.9 g of the desired product, m.p. (decomposed at 257°–8°). This compound conforms to Formula II where $R^1$ and $R^2$ are —OCH$_3$, $R^3$ is H and $R^4$ is —CH$_2$CH$_3$.

Anal. Calcd for $C_{18}H_{26}N_2O_3$·HCl: C, 60.92; H, 7.67; N, 7.89; Found: C, 60.97; H, 7.55; N, 7.67.

EXAMPLE VII 1,3,4,6,7,11b-Hexahydro-9,10-dimethoxy-2-(4-methoxybenzoylamino)-2H-benzo[a]quinolizine hydrochloride (TR-3819)

A mixture of 2-amino-1,3,4,6,7,11b-hexahydro-9,10-dimethoxy-2H-benzo[a]quinolizine (5 g, 0.019 mole), 200 ml of benzene and 25 ml of 20% NaOH was cooled 10° and a solution of 4-methoxy benzoyl chloride (3.3 g, 0.019 mole) in benzene was added dropwise with stirring. The mixture was stirred in the cold for 30 minutes and at room temperature for 1 hour. The solid was collected after removal of the solvent and chromatographed over silica gel using benzene-methanol (6:1) as eluant. The major fraction (3.8 g) was converted to the HCl salt with hydrogen chloride in 2-propanol. The solvent was removed from the salt in vacuo whereupon the salt was twice recrystallized from methanol-ether, once from 2-propanol and again from absolute ethanol-ethyl acetate to yield 0.8 g of the desired product m.p. (decomposed at 244°–6°). This compound conforms to Formula II where $R^1$ and $R^2$ are $-OCH_3$, $R^3$ is H and $R^4$ is

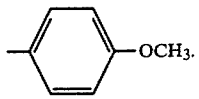

Anal. Calcd for $C_{23}H_{28}N_2O_4 \cdot HCl$: C, 63.80; H, 6.75; N, 6.47; Found: C, 63.19; H, 6.56; N, 6.40.

EXAMPLE VIII 2-(3-Chlorobenzoylamino)-1,3,4,6,7,11b-hexahydro-9,10-dimethoxy-2H-benzo[a]quinolizine hydrochloride (TR-3823)

A mixture of 2-amino-1,3,4,6,7,11b-hexohydro-9, 10-dimethoxy-2H-benzo[a]quinolizine (5 g, 0.019 mole), 150 ml of benzene and 50 ml of 20% NaOH was cooled to below 10° at which point 3-chlorobenzoyl chloride (3.4 g 0.019 mole) was added dropwise with stirring. The mixture was stirred in the cold for 1 hour whereupon the solid was collected by filtration and chromatographed over silica gel using benzene-methanol (6:1) as eluant. The major fraction (3.8 g) was converted to the HCl salt with hydrogen chloride in 2-propanol and was recrystallized from methanol-2-propanol and again from 2-propanol to yield 3.0 g of the desired product, m.p. (decomposed at 262°–4°). This compound conforms to Formula II where $R^1$ and $R^2$ are $-OCH_3$, $R^3$ is H and $R^4$ is

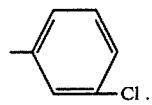

Anal. Calcd for $C_{22}H_{25}ClN_2O_3 \cdot HCl$: C, 60.41; H, 5.99; N, 6.40; Found: C, 60.46; H, 5.98; N, 6.20.

EXAMPLE IX 1,3,4,6,7,11b-Hexahydro-9,10-dimethoxy-2-(3-methoxybenzoylamino)-2H-benzo[a]quinolizine hydrochloride (TR-3832)

A mixture of 2-amino-1,3,4,6,7,11b-hexahydro-9, 10-dimethoxy-2H-benzo[a]quinolizine (5 g, 0.019 mole), 150 ml of benzene and 30 ml of 20% NaOH was cooled to below 10° whereupon 3-methoxy benzoyl chloride (3.3 g, 0.02 mole) was added dropwise with stirring. The mixture was stirred in the cold for 1 hour and filtered to remove the solid whereupon the solid was chromatographed over silica gel using benzene-methanol (6:1) as eluant. The major fraction (4.1 g) was converted to the HCl salt with hydrogen chloride in 2-propanol and the solvent was removed in vacuo. The salt was crystallized from methanol-ether to yield 1.5 g of the desired product, m.p. (decomposed at 217°–9°). This compound conforms to Formula II where $R^1$ and $R^2$ are $-OCH_3$ $R^3$ is H and $R^4$ is

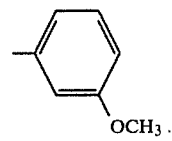

Anal. Calcd for $C_{23}H_{28}N_2O_4 \cdot HCl \cdot H_2O$: C, 61.25; H, 6.93; N, 6.21; Found: C, 61.53; H, 6.51; N, 6.04.

EXAMPLE X 1,3,4,6,7,11b-Hexahydro-9,10-dimethoxy-2-(4-nitrobenzoylamino)-2H-benzo[a]quinolizine hydrochloride (TR-3839)

A mixture of 2-amino-1,3,4,6,7,11b-hexahydro-9, 10-dimethoxy-2H-benzo[a]quinolizine (7 g), 200 ml of toluene and 50 ml of 20% NaOH was cooled to below 10° and a solution of 4-nitrobenzoyl chloride (5 g) in toluene was added dropwise with stirring. The mixture was stirred in the cold for 1 hour and allowed to come to room temperature whereupon the solid was collected by filtration and chromatographed over silica gel using ethyl acetate-methanol (6:1) as eluant. The major fraction (5.3 g) was converted to the HCl salt with hydrogen chloride in 2-propanol and the solvent was removed in vacuo. The salt was crystallized from methanol-ether to yield 1.5 g of the desired product, m.p. (decomposed at 269° –70°). This compound conforms to Formula II where $R^1$ and $R^2$ are $-OCH_3$, $R^3$ is H and $R^4$ is

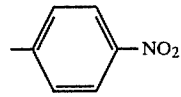

Anal. Calcd for $C_{22}H_{25}N_3O_5 \cdot HCl$: C, 59.00; H, 5.85; N, 9.38; Found: C, 58.90; H, 5.85; N, 9.45

EXAMPLE XI 2-(4-Aminobenzoylamino)-1,3,4,6,7,11b-hexahydro-9,10-dimethoxy-2H-benzo[a]quionlizine fumarate (TR-3840)

A solution of 2-(4-nitrobenzoylamino)-1,3,4,6,7,11b-hexahydro-9,10-dimethoxy-2H-quinolizine (4.5 g, 0.01 mole) in 200 ml of glacial acetic acid and 0.2 g of 10% Pd/C was hydrogenated on a Paar apparatus. The concentrate was dissolved in chloroform, washed with dilute NaOH, dried over MgSO4, concentrated in vacuo and chromatographed over silica gel using ethyl acetate-methanol (4:1) as eluant. The major fraction (2.6 g) and fumaric acid (2 g) were dissolved in methanol and the salt crystallized by the addition of ether. The salt was recrystallized from 2-propanol-ether and again from methanol-ether to yield 1.1 g of the desired product, m.p. (decomposed at 174°-6°). This compound conforms to Formula II where $R^1$ and $R^2$ are —OCH$_3$, $R^3$ is H and R$_4$ is

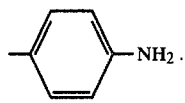

Anal. Calcd for C$_{22}$H$_{27}$N$_3$O$_3$·C$_4$H$_4$O$_4$H$_2$O; C, 60.57; H, 6.45; N, 8.15; Found; C, 60.47; H, 6.42; N, 8.47.

EXAMPLE XII 2-(4-Acetylaminobenzoylamino)-1,3,4,6,7,11b-hexahydro-9,10-dimethoxy-2H-benzo[a]quinolizine oxalate (TR-3859)

A mixture of 1,3,4,6,7,11b-hexahydro-9, 10-dimethoxy-2-(4-nitrobenzoylamino)-2H-benzo[a]quinolizine (4.5 g, 0.01 mole), acetic anhydride (2 ml), glacial acetic acid (200 ml) and 10% Pd/C was hydrogenated on a Parr apparatus. The concentrate was dissolved in chloroform, washed with dilute NaOH, dried over MgSO$_4$, reconcentrated in vacuo and chromatographed over silica gel using toluene-methanol (5:1) as the eluant. The major fraction containing two spots on TLC was rechromatographed over silica gel using chloroform-ethanol (9:1) as eluant. The major fraction (2.2 g) and 1.5 g of oxalic acid were dissolved in methanol and the salt precipitated by the addition of ether. The salt was recrystallized from methanol-ether to yield 1.1 g of the desired product, m.p. (decomposed at 215°-6°). This compound conforms to Formula II where $R^1$ and $R^2$ are —OCH$_3$, $R^3$ is H and $R^4$ is

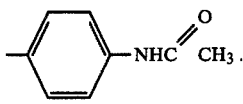

Anal. Calcd for C$_{24}$H$_{29}$N$_3$O$_4$·C$_2$H$_2$O$_4$: C, 60.82; H, 6.09; N, 8.18; Found: C, 60.73; H, 6.00; N, 8.11.

EXAMPLE XIII 1,3,4,6,7,11b-Hexahydro-9,10-dimethoxy-2-(3,4,5-trimethoxybenzoylamino)-2H-benzo[a]quinolizine hydrochloride (TR-3895)

A solution of 3,4,5-trimethoxy benzoyl chloride (13 g) in pyridine was added dropwise to 2-amino-1,3,4,6,7,11b-hexahydro-9,10-dimethoxy-2H-benzo[a]quinolizine (13 g) in 200 ml of pyridine, and the solution was warmed at 60°-70° for 30 minutes and poured into ice water. The mixture was extracted with chloroform and the extracts dried over MgSO$_4$, concentrated in vacuo and the concentrated material chromatographed over silica gel using ethyl acetate-methanol-chloroform (4:1:0.5) as eluant. The major fraction (9.9 g) was converted to the HCl salt with hydrogen chloride in a mixture of 2-propanol, methanol and ethyl acetate, isolated as a solid and recrystallized from methanol-ethyl acetate and again from methanol to yield 3.6 g of the desired product, m.p. (decomposed at 259°-61°). This compound conforms to Formula II where $R^1$ and $R^2$ are —OCH$_3$, $R^3$ is H and $R^4$ is

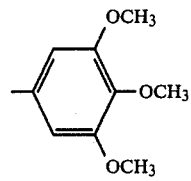

Anal. Calcd for C$_{25}$H$_{32}$N$_2$O$_6$·HCl: C, 60.90; H, 6.75; N, 5.68; Found: C, 60.23; H, 6.76; N, 5.69.

EXAMPLE XIV 1,3,4,6,7,11b-Hexahydro-9,10-dimethoxy-2-(4-methylbenzoylamino)-2H-benzo[a]quinolizine hydrochloride (TR-3896)

To a cold mixture of 2-amino-1,3,4,6,7,11b-hexahydro-9,10-dimethoxy-2H-benzo[a]quinolizine (9 g, 0.034 mole) in 300 ml of toluene and 75 ml of 20% NaOH was added dropwise p-toluoyl chloride (6 g, 0.035 mole). The mixture was stirred in the cold for 1 hour and allowed to come to room temperature. The solid was collected by filtration and the toluene layer concentrated in vacuo whereupon the solid and concentrate were combined and chromatographed over silica gel using ethyl acetate-methanol (4:1) as eluant. The major fraction (6.2 g) was converted to the HCl salt with hydrogen chloride in a mixture of 2-propanol, methanol and ethyl acetate, isolated and twice recrystallized from methanol-ethyl acetate to yield 3.2 g of the desired product, m.p. (decomposed at 268°-70°). This compound conforms to Formula II where $R^1$ and $R^2$ are —OCH$_3$, $R^3$ is H and $R^4$ is

Anal. Calcd for C$_{23}$H$_{28}$N$_2$O$_3$·HCl; C, 66.26; H, 7.01; N, 6.72; Found: C, 66.14; H, 7.26; N, 6.88.

EXAMPLE XV 2-(3,4-Dichlorobenzoylamino)-1,3,4,6,7,11b-hexahydro-9, 10-dimethoxy-2H-benzo[a]quinolizine hydrochloride (TR-3898)

A mixture of 3,4-dichlorobenzoic acid (6.5 g) and 25 ml of SOCl$_2$ were refluxed for 3 hours and concentrated in vacuo. The concentrate was dissolved in 10 ml of toluene and added dropwise to a cold mixture of 2-amino-1,3,4,6,7,11b-hexahydro-9,10-dimethoxy-2H-benzo[a]quinolizine (8 g, 0.03 mole) in 200 ml of toluene and 75 ml of 20% NaOH. The mixture was stirred in the cold for 1 hour whereupon the solid material was collected by filtration and chromatographed over silica gel using ethyl acetate-methanol-chloroform (7:2:1) as eluant. This major fraction (6.2 g) was converted to the HCl salt with hydrogen chloride in 2-propanol and methanol, isolated by evaporation of the solvent and recrystallized from methanol-ethyl acetate to yield 3.8 g of the desired product, m.p. (decomposed at 271°-3°). This compound conforms to Formula II where $R^1$ and $R^2$ are —OCH$_3$, $R^3$ is H and $R^4$ is

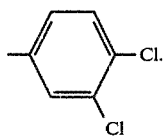

Anal. Calcd for $C_{22}H_{24}Cl_2N_2O_3 \cdot HCl$: C, 56.01; H, 6.34; N, 5.94; Found: C, 56.27; H, 5.37; N, 5.90.

EXAMPLE XVI 2-(4-Chlorobenzoylamino)-1,3,4,6,7,11b-hexahydro-9,10-dimethoxy-2H-benzo[a]quinolizine hydrochloride (TR-3902)

A mixture of 2-amino-1,3,4,6,7,11b-hexahydro-9,10-dimethoxy-2H-benzo[a]quinolizine (8 g, 0.03 mole), 200 ml of toluene and 80 ml of 20% NaOH was cooled to 10° in an ice bath at which point 4-chlorobenzoyl chloride (5.5 g, 0.03 mole) was added dropwise with stirring. The mixture was stirred in the cold for 1 hour whereupon the solid was collected by filtration and chromatographed over silica gel using ethyl acetate-methanol-chloroform (3:1:1) as eluant. The major fraction (6.2 g) was converted to the HCl salt with hydrogen chloride in 2-propanol-ethyl acetate and was recrystallized from methanol-ethyl acetate twice to yield 4.2 g of the desired product, m.p. (decomposed at 253°–4°). This compound conforms to Formula II where $R^1$ and $R^2$ are —OCH$_3$, $R^3$ is H and $R^4$ is

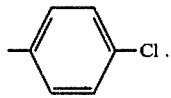

Anal. Calcd for $C_{22}H_{25}ClN_2O_3 \cdot HCl$: C, 60.41; H, 5.99; N, 6.40; Found: C, 59.83; H, 5.85; N, 6.35.

EXAMPLE XVII 1,3,4,6,7,11b-Hexahydro-2-(4-methoxybenzoylamino)-2H-benzo[a]quinolizine hydrochloride (TR-3916)

A mixture of 2-amino-1,3,4,6,7,11b-hexahydro-2H-benzo[a]quinolizine (8 g, 0.039 mole), 200 ml of toluene and 50 ml of 20% NaOH was cooled below 10° in an ice bath and p-anisoylchloride (6.8 g, 0.039 mole) was added dropwise with stirring. The mixture was stirred in the cold for 1 hour whereupon the solid product was collected by filtration and recrystallized from aqueous methanol to yield 6.5 g of the free base of the desired product, m.p. 211°–3°. The free base was converted to the HCl salt with hydrogen chloride in 2-propanol and concentrated in vacuo. The concentrate was crystallized from acetone and recrystallized from methanol-ether to yield 5.0 g of the salt, m.p. (decomposed at 210°–2°). This compound conforms with Formula II where $R^1$ and $R^2$ are H, $R^3$ is H and $R^4$ is Anal. Calcd for $C_{21}H_{24}N_2O_2 \cdot HCl$: C, 67.64; H, 6.76; N, 7.52; Found: C, 67.36; H, 6.82; N, 7.36.

EXAMPLE XVIII 1,3,4,6,7,11b-Hexahydro-9,10-dimethoxy-2-(4-methoxyphenylacetylamino)-2H-benzo[a]quinolizine hydrochloride (TR-3925)

To a cold mixture of 2-amino-1,3,4,6,7,11b-hexahydro-9,10-dimethoxy-2H-benzo[a]quinolizine (7.3 g, 0.029 mole), 200 ml of toluene and 50 ml of 20% NaOH was added dropwise 5.5 g of 4-methoxyphenylacetyl chloride. The resulting mixture was stirred in the cold for 1 hour whereupon the solid product was collected by filtration and chromatographed over silica gel using ethyl acetate-methanol (3:1) as eluant. The major fraction (3.4 g) was converted to the HCl salt with hydrogen chloride in 2-propanol and concentrated by removal of the solvent in vacuo. The concentrate was crystallized from methanol-ether and recrystallized from methanol-ether to yield 2.2 g of the desired product, m.p. (decomposed at 188°–90°). This compound conforms to Formula II where $R^1$ and $R^2$ are —OCH$_3$, $R^3$ is H and $R^4$ is

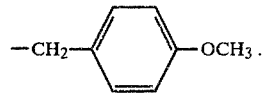

Anal. Calcd for $C_{24}H_{30}N_2O_4 \cdot HCl$: C, 64.49; H, 6.99; N, 6.27; Found: C, 64.17; H, 6.85; N, 6.40.

EXAMPLE XIX 2-(2-Furanylcarbozylamino)-1,3,4,6,7,11b-hexahydro-9,10-dimethoxy-2H-benzo[a]quinolizine hydrochloride (TR-3934)

To a cold stirred mixture of 2-amino-1,3,4,6,7,11b-hexahydro-9,10-dimethoxy-2H-benzo[a]quinolizine (7.3 g, 0.028 mole) in 200 ml of toluene and 100 ml of 20% NaOH was added dropwise 3.7 g, (0.028 mole) of 2-furoyl chloride. The resulting mixture was stirred in the cold for 2 hours whereupon the solid product was collected by filtration and chromatographed over silica gel using ethyl acetate-methanol-chloroform (8:2:1). The major fraction (4.7 g) was converted to the HCl salt with hydrogen chloride in 2-propanol and the mixture was concentrated by removal of the solvent in vacuo. The concentrate was crystallized and recrystallized from absolute ethanol-ether to yield 2.9 g of the desired product, m.p. (decomposed at 234°–6°). This compound conforms to Formula II where $R^1$ and $R^2$ are —OCH$_3$, $R^3$ is H and $R^4$ is

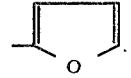

Anal. Calcd for $C_{20}H_{24}N_2O_4 \cdot HCl$: C, 58.48; H, 6.62; N, 6.82; Found: C, 58.77; H, 6.26; N, 6.87.

EXAMPLE XX 1,3,4,6,7,11b-Hexahydro-9,10-dimethoxy-2-(4-phenylmethoxybenzoylamino)-2H-benzo-[a]quinolizine hydrochloride (TR-3935)

To a stirred solution of 2-amino-1,3,4,6,7,11b-hexahydro-9,10-dimethoxy-2H-benzo[a]quinolizine (15 g, 0.056 mole) in 300 ml of pyridine was added in portions 24 g of 4-benzyloxybenzoic anhydride. The resulting mixture was stirred on a steam bath for 2 hours and poured into ice water containing 100 ml of 20% NaOH whereupon a solid precipitated. The solid was collected and recrystallized from aqueous dimethylformamide-methanol to yield 16 g of free base. The free base was chromatographed on silica gel using chloroform-methanol (9:1) as eluant. The major fraction (3.6 g), m.p. 236°-8°, was converted to the HCl salt with hydrogen chloride and a mixture of 2-propanol, methanol and ethyl acetate and recrystallized from methanol-ethyl acetate to yield 2.0 g of the desired product m.p. (decomposed at 258°-60°). This compound conforms to Formula II where $R^1$ and $R^2$ are —$OCH_3$, $R^3$ is H and $R^4$ is

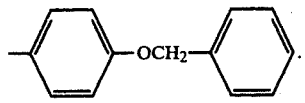

Anal. Calcd for $C_{29}H_{32}N_2O_4 \cdot HCl$: C, 68.42; H, 6.53; N, 5.50; Found: C, 68.66; H, 6.60; N, 5.44.

EXAMPLE XXI 1,3,4,6,7,11b-Hexahydro-9,10-dimethoxy-2-(2-methoxybenzoylamino)-2H-benzo[a]quinolizine hydrochloride (TR-3936)

To a cold mixture of 2-amino-1,3,4,6,7,11b-hexahydro-9,10-dimethoxy-2H-benzo[a]quinolizine, (7 g, 0.026 mole) in 200 ml of toluene and 75 ml of 20% NaOH, was added dropwise 4.8 g of 2-anisoyl chloride in toluene. The mixture was stirred in the cold for 1 hour after which the toluene layer was collected, dried over $MgSO_4$ and concentrated in vacuo. The concentrate was chromatographed over silica gel using ethyl acetate-methanol (4:1) as eluant. The major fraction (6.5 g) was converted to the HCl salt with hydrogen chloride in 2-propanol and the mixture concentrated by removal of the solvent in vacuo. The salt was crystallized from acetone and twice recrystallized from methanol-ethyl acetate to yield 3.0 g of the desired product, m.p. (decomposed at 243°-4°). This compound conforms to Formula II where $R^1$ and $R^2$ are —$OCH_3$, $R^3$ is H and $R^4$ is

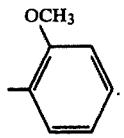

Anal. Calcd for $C_{23}H_{28}N_2O_4 \cdot HCl$: C, 63.80; H, 6.75; N, 6.47; Found: C, 63.63; H, 6.61; N, 6.27.

EXAMPLE XXII 1,3,4,6,7,11b-Hexahydro-9,10-dimethoxy-2-[3-(4-methoxyphenyl)propanoylamino]-2H-benzo[a]quinolizine hydrochloride (TR-3937)

To a mixture of 2-amino-1,3,4,6,7,11b-hexahydro-9,10-dimethoxy-2H-benzo[a]quinolizine (7 g, 0.026 mole) in 200 ml of toluene and 50 ml of 20% NaOH was added dropwise 5.5 g of 3-(4-methoxy)propionyl chloride. The mixture was stirred in the cold for 1 hour whereupon the solid product was collected, dried and recrystallized from 2-propanol-petroleum ether to yield 6 g of free base. The free base was chromatographed over silica gel using ethyl acetate-methanol-chloroform (15:5:1) as the eluant. The major fraction (5.5 g) was converted to the HCl salt with hydrogen chloride in 2-propanol. The excess solvent was removed by concentration in vacuo. The concentrate was twice recrystallized from methanol-ethyl acetate and twice from 2-propanol to yield 1.4 g of the desired product, m.p. (decomposed at 235°-7°). This compound conforms to Formula II where $R^1$ and $R^2$ are —$OCH_3$, $R^3$ is H and $R^4$ is

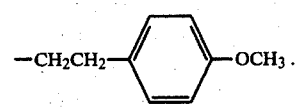

Anal. Calcd for $C_{25}H_{32}N_2O_4 \cdot HCl$: C, 65.14; H, 7.22; N, 6.08; Found: C, 64.93; H, 7.20; N, 6.06.

EXAMPLE XXIII 2-(4-Fluorobenzoylamino)-1,3,4,6,7,11b-hexahydro-9,10-dimethoxy-2H-benzo[a]quinolizine hydrochloride (TR-3942)

To a cold mixture of 2-amino-1,3,4,6,7,11b-hexahydro-9,10-dimethoxy-2H-benzo[a]quinolizine, (7 g, 0.026 mole) in 200 ml of toluene and 50 ml of 20% NaOH, was added dropwise 4.5 g of 4-fluorobenzoyl chloride. The mixture was stirred in the cold for 1 hour and at room temperature for 1 hour. The resulting solid product was collected and chromatographed over silica gel using ethyl acetate-methanol-chloroform (3:1:1) as eluant. The major fraction (5.0 g) was converted to the HCl salt with hydrogen chloride in 2-propanol and ether, isolated by removal of the solvent and recrystallized from methanol-ether to yield 2.3 g of the desired product, m.p. (decomposed at 257°-8°). This compound conforms to Formula II where $R^1$ and $R^2$ are —$OCH_3$, $R^3$ is H and $R^4$ is

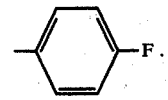

Anal. Calcd for $C_{22}H_{25}FN_2O_3 \cdot HCl$: C, 62.78; H, 6.23; N, 6.66; Found: C, 62.70; H, 6.20; N, 6.76.

EXAMPLE XXIV 1,3,4,6,7,11-bHexahydro-2-(4-hydroxybenzoylamino)-9,10-dimethoxy-2H-benzo[a]quinolizine hydrochloride (TR-3967)

A mixture of 2-(4-benzyloxybenzoylamino)-1,3,4,6,7,11b-hexahydro-9,10-dimethoxy-2H-benzo[a]quinolizine HCl (9 g), 200 ml of acetic acid, 10 ml of 20% HCl and 10% Pd/C was hydrogenated on a Paar apparatus for 4 days. The mixture was filtered and concentrated in vacuo whereupon the salt concentrate was crystallized and recrystallized from methanol-ethyl acetate to yield 3.6 g of the desired product, m.p. (decomposed at 256.9°). This compound conforms to Formula II where $R^1$ and $R^2$ are —$OCH_3$, $R_3$ is H and $R_4$ is

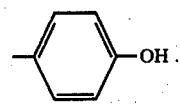

Anal. Calcd for $C_{22}H_{26}N_2O_4 \cdot HCl$: C, 63.08; H, 6.50; N, 6.69; Found: C, 63.12; H, 6.89; N, 6.58.

EXAMPLE XXV 1,3,4,6,7,11b-Hexahydro-9,10-dimethoxy-2-[(4-piperidyl)acetylamino]-2H-benzo[a]quinolizine dihydrochloride (TR-3977)

A solution of 2-amino-1,3,4,6,7,11b-hexahydro-9,10-dimethoxy-2H-benzo[a]quinolizine-2HCl.H$_2$O (7.6 g, 0.029 mole) in 200 ml of toluene and 50 ml of 20% NaOH was cooled to 15° and chloroacetyl chloride (3.3 g) was added dropwise. The mixture was stirred in the cold for 1 hour whereupon the solid product was collected and dried. A mixture of this solid (7 g), piperidine (5 ml), dimethylformamide (150 ml) and 15 g of Na$_2$CO$_3$ was stirred on a steam bath for four hours, filtered and the filtrate concentrated in vacuo. The concentrate was chromatographed over silica gel using toluene-methanol-chloroform (8:2:1) as eluant to yield 2.7 g of free base. The free base was converted to the HCl salt with hydrogen chloride in 2-propanol-ethyl acetate, isolated by removal of the solvent and recrystallized three times from methanol-ethyl acetate to yield 1.8 g of the desired product, m.p. (decomposed at 233°–5°). This compound conforms to Formula II where R$^1$ and R$^2$ are —OCH$_3$, R$^3$ is H and R$^4$ is

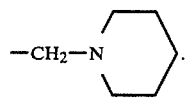

Anal. Calcd for C$_{22}$H$_{33}$N$_3$O$_3$.2HCl: C, 57.38; H, 7.66; N, 9.12; Found: C, 57.04; H, 7.73; N, 9.24.

EXAMPLE XXVI 2-(4-Ethoxybenzoylamino)-1,3,4,6,7,11b-hexahydro-9,10-dimethoxy-2H-benzo[a]quinolizine hydrochloride (TR-3979)

A mixture of 2-amino-1,3,4,6,7,11b-hexahydro-9,10-dimethoxy-2H-benzo[a]quinolizine (7.1 g, 0.027 mole), 200 ml of toluene and 50 ml of 20% NaOH was cooled in an ice bath while 4-ethoxybenzoyl chloride (5.5 g) was added dropwise. The mixture was stirred in the cold for 1 hour. The solid product was collected by filtration, dissolved in chloroform and the chloroform dried over MgSO$_4$ and concentrated in vacuo. The concentrate was chromatographed over silica gel using toluene-methanol-chloroform (5:1:1) as eluant to yield 5.5 g of the free base as the major isomer. This material was recrystallized from aqueous methanol to yield 5.0 g of the free base, m.p. 227°–9°. The free base was converted to the HCl salt with hydrogen chloride in 2-propanol-ethyl acetate and again from methanol to yield 2.9 g of the desired product, m.p. (decomposed at 245°–7°; softens ca. 190°). This compound conforms to Formula II where R$^1$ and R$^2$ are OCH$_3$, R$^3$ is H and R$^4$ is

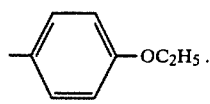

Anal. Calcd for C$_{24}$H$_{30}$N$_2$O$_4$.HCl: C, 64.49; H, 6.99; N, 6.27; Found: C, 64.43; H, 7.00; N, 6.33.

EXAMPLE XXVII 1,3,4,6,7,11b-Hexahydro-9,10-dimethoxy-2-(N-methoxybenzoyl-N-methylamino)-2H-benzo[a]quinolizine hydrochloride (TR-3988)

A mixture of 1,3,4,6,7,11b-hexahydro-9,10-dimethoxy-2-methylamino-2H-benzo[a]quinolizine (8.5 g, 0.03 mole) and 50 ml of 20% NaOH in 250 ml of toluene was cooled in an ice bath and p-anisoyl chloride (6 g) was added dropwise. The mixture was stirred in the cold for 1 hour and the toluene layer separated and concentrated in vacuo. The concentrate was chromatographed over silica gel using ethyl acetate-methanol-chloroform (4:1:1) as eluant. The main fraction (7.0 g) was crystallized from 2-propanol-petroleum ether to yield 6.5 g of the free base, m.p. 156°–8°. The free base was converted to the HCl salt with hydrogen chloride in 2-propanol and ethyl acetate, isolated by filtration and recrystallized from methanol-ethyl acetate to yield 4.1 g of the desired product, m.p. (decomposed at 258°–9°). This compound conforms to Formula II where R$^1$ and R$^2$ are —OCH$_3$, R$^3$ is —CH$_3$ and R$^4$ is

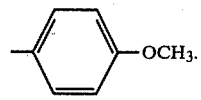

Anal. Calcd for C$_{24}$H$_{30}$N$_2$O$_4$.HCl: C, 64.49; H, 6.99; N, 6.27; Found: C, 64.70; H, 6.95; N, 6.38.

EXAMPLE XXVIII 1,3,4,6,7,11b-Hexahydro-2-(4-methoxybenzoylamino)-9,10-methylenedioxy-2H-benzo[a]quinolizine hydrochloride (TR-3983)

A mixture of 2-amino-1,3,4,6,7,11b-hexahydro-9,10-methylenedioxy-2H-benzo[a]quinolizine (6.5 g, 0.026 mole), 20% NaOH (50 ml) and 200 ml of toluene was cooled in an ice bath and p-anisoyl chloride (4.6 g) was added dropwise. The mixture was stirred in the cold for one hour whereupon the solid was collected and recrystallized from aqueous methanol-DMF. The free base was converted to the HCl salt with hydrogen chloride in a mixture of 2-propanol and ethyl acetate. The resulting solid was collected and twice recrystallized from methanol-ethyl acetate to yield 3.3 g of the desired product, m.p. (decomposed at 228°–30°). This product conforms to Formula II where R$^1$ and R$^2$ combined are

R$^3$ is H and R$^4$ is

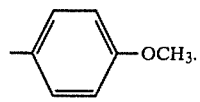

Anal. Calcd for C$_{22}$H$_{24}$N$_2$O$_4$.HCl: C, 63.38; H, 6.04; N, 6.72; Found: C, 63.24; H, 6.09; N, 6.76.

EXAMPLE XXIX 1,3,4,6,7,11b-Hexahydro-2-(benzoylamino)-9,10-dimethoxy-2H-benzo[a]quinolizine hydrochloride (TR-3807)

A mixture of 2-amino-1,3,4,6,7,11b-hexahydro-9,10-dimethoxy-2H-benzo[a]quinolizine (5.0 g., 0.019 mole), 20% NaOH (25 ml) and 150 ml of benzene was cooled in an ice bath and benzoyl chloride (2.7 g, 0.019 mole) in 10 ml of benzene was added dropwise with stirring. The mixture was stirred in the cold for 30 minutes and at room temperature for 1 hour. The solid was collected, dissolved in chloroform, washed with water, dried (MgSO₄) and concentrated in vacuo. The residue (5 g) was chromatographed over silica gel eluting with benzene-methanol (9:1). The free base (3.7 g) was converted to the HCl salt with hydrogen chloride in a mixture of 2-propanol and methanol. The solution was concentrated in vacuo and the residue was crystallized from methanol-ether. The resulting solid was recrystallized from ethanol-ether to yield 3.0 g of the desired product, m.p. 250°-1°. This product comforms to Formula II where $R^1$ and $R^2$ are $-OCH_3$, $R^3$ is H and $R^4$ is

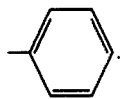

Anal. Calcd for $C_{22}H_{27}ClN_2O_3$: C, 65.59, H, 6.75; N, 6.95. Found: C, 65.37; H, 6.72; N, 6.84.

EXAMPLE XXX

Determination of the Anti-Hypertensive Effects of the Compounds of the Present Invention Antihypertensive activity was determined in rats and dogs. Rats were made hypertensive by applying a figure of eight ligature to one kidney and removing the contralateral kidney two weeks later. At least four weeks after the second operation the animals were subjected to indirect systolic blood pressure measurements with an occluding cuff and pulse sensor system applied to the tail. Pressure measurements were made before and 1, 2, 4, 6 and 8 hours after oral administration of the test compounds at a dose of 31 mg/kg. Each compound was tested in 5 or 10 rats. Statistical significance or differences between control and post treatment values was determined by Wilcoxon's signed rank test (F. Wilcoxon and R. A. Wilcox, Some Rapid Approximate Statistical Procedures, Lederle Laboratories, Pearl River, 1964). The results of this study are present in Table I. Compounds significantly lowering blood pressure in rats were subsequently tested in dogs made hypertensive by unilateral renal artery constriction and contralateral nephrectomy. Systolic and diastolic blood pressure were determined indirectly with an occluding cuff and pulse sensor system applied to the tail of the animals. The resultant arterial pulsations were inscribed in a suitable recorder and were counted to determine heart rate. Mean blood pressure was calculated by adding ⅓ of the differential pressure (systolic minus diastolic) to the diastolic pressure. Pressure and heart rate measurements were made before and 1, 2, 4, 6 and 8 hours after oral administration of the test compounds at a dose of 10 mg/kg. All compounds without increasing heart rate were tested in additional animals. The results of this study are presented in Table I.

TABLE I

Antihypertensive Activity of Benzoquinolizines in the Rat Test Dose: 31 mg/kg, p.o.

| Ex. No. | TR | Number of Rats | Initial BP, mmHg | Change in Systolic Blood Pressure, mmHg, at | | | | |
|---|---|---|---|---|---|---|---|---|
| | | | | 1 hr | 2 hr | 4 hr | 6 hr | 8 hr |
| 1 | 3413 | 10 | 212 | −39 | −44* | −22* | +1 | +2 |
| 2 | 3697 | 10 | 199 | −77* | −96* | −103* | −65* | −49* |
| 3 | 3804 | 10 | 184 | −38* | −27* | −25* | −3 | −2 |
| 4 | 3805 | 5 | 196 | −16 | +7 | −10 | +17 | −18 |
| 5 | 3807 | 10 | 195 | −14 | −1 | +1 | +17 | +8 |
| 6 | 3813 | 10 | 192 | −62* | −47* | −39* | −14 | −9 |
| 7 | 3819 | 10 | 189 | −25* | −24* | −20* | −10 | −13* |
| 8 | 3823 | 10 | 190 | −34* | −15 | −14 | −10 | −4 |
| 9 | 3832 | 10 | 188 | −19* | 0 | 0 | +2 | +5 |
| 10 | 3839 | 10 | 187 | −34* | −27* | −27* | −16* | +2 |
| 11 | 3840 | 10 | 187 | −24* | −16* | −13* | −3 | +17 |
| 12 | 3859 | 10 | 198 | −5 | +1 | −3 | +1 | +12 |
| 13 | 3895 | 10 | 190 | −52* | −53* | −60* | −63* | −61* |
| 14 | 3896 | 10 | 202 | −36* | −19* | −19* | −7 | +3 |
| 15 | 3898 | 10 | 189 | −19* | −22* | −18* | −15* | −4 |
| 16 | 3902 | 10 | 198 | −32* | −31* | −17 | −7 | −7 |
| 17 | 3916 | 10 | 192 | −37* | −25* | −27* | −8 | −1 |
| 18 | 3925 | 10 | 188 | −14* | −12* | −12 | −4 | 0 |
| 19 | 3934 | 10 | 188 | −18* | −11* | −7 | −7 | +5 |
| 20 | 3935 | 5 | 205 | −5 | −5 | −5 | −5 | +1 |
| 21 | 3936 | 5 | 191 | −7 | −5 | +3 | +4 | +3 |
| 22 | 3937 | 5 | 190 | +6 | +4 | +7 | +5 | +9 |
| 23 | 3942 | 5 | 206 | −13 | −11 | −5 | −4 | +1 |
| 24 | 3967 | 10 | 198 | −25* | −18* | −19* | −8 | −1 |
| 25 | 3977 | 10 | 207 | −7 | −7 | −1 | +6 | +5 |
| 26 | 3979 | 10 | 204 | −11* | −13 | −14 | −8 | 0 |
| 27 | 3988 | 10 | 214 | −61* | −56* | −37* | −14 | −10 |
| 28 | 3983 | 10 | 198 | −20* | −19* | −10 | −3 | +1 |
| 29 | 3807 | 10 | 195 | −14 | −1 | +1 | +17 | +8 |

*Statistically significant change from control.

From the above table, it can be determined that about two thirds of the 2-amido-hexahydrobenzo[a]quinolizines prepared as previously described possess statistically significant anti-hypertensive activity.

The determination that one in three of these structurally related compounds does not function as an anti-hypertensive agent highlights the unpredictability of the utility of these compounds.

In the dog test, both blood pressure and heart rate were measured after administration of the compound. In general, the criterion for useful activity in this test is a decrease in blood pressure of at least 20 mmHg and an increase in heart rate of less than 20 beats/min. Referring to the following Table II, it can be determined that TR-3804, TR-3819, TR-3898, and TR-3902 meet this criterion whereas the other compounds whose preparatin is disclosed herein do not.

TABLE II

Antihypertensive and Heart Rate Effects of Amide Benzoquinolizines in the Dog. Test Dose: 10 mg/kg,p.o.

| TR | Number of Dogs | Parameter | Initial Value | Change in Parameter at | | | | |
|---|---|---|---|---|---|---|---|---|
| | | | | 1 hr | 2 hr | 4 hr | 6 hr | 8 hr |
| 3413 | 1 | MBP, mmHg | 142 | −6 | −14 | −11 | −5 | +2 |
| | | HR, b/min | 76 | +40 | +36 | +36 | +8 | +16 |
| 3697 | 1 | MBP | 134 | +3 | +2 | −8 | +7 | +4 |
| | | HR | 112 | +56 | +28 | +36 | +16 | +12 |
| 3804 | 3 | MBP | 139 | −38 | −27 | −21 | −19 | −8 |
| | | HR | 77 | +12 | +15 | +20 | +6 | +15 |
| 3813 | 1 | MBP | 135 | −39 | −9 | −21 | −11 | −26 |
| | | HR | 80 | +4 | +8 | +20 | +20 | +20 |
| 3819 | 6 | MBP | 138 | −13 | −14 | −22 | −3 | −10 |

TABLE II-continued
Antihypertensive and Heart Rate Effects of Amide Benzoquinolizines in the Dog. Test Dose: 10 mg/kg,p.o.

| TR | Number of Dogs | Parameter | Initial Value | 1 hr | 2 hr | 4 hr | 6 hr | 8 hr |
|---|---|---|---|---|---|---|---|---|
| 3823 | 1 | HR | 83 | +1 | +4 | +4 | +4 | +2 |
|  |  | MBP | 128 | −8 | −8 | −6 | +7 | +7 |
| 3832 | 1 | HR | 88 | +4 | 0 | −8 | +4 | 0 |
|  |  | MBP | 156 | +3 | −4 | −34 | −2 | −3 |
| 3839 | 1 | HR | 132 | −4 | +8 | +8 | +20 | +20 |
|  |  | MBP | 135 | −33 | −38 | −46 | +8 | +1 |
| 3840 | 1 | HR | 88 | +40 | +28 | +36 | +40 | +12 |
|  |  | MBP | 133 | −20 | −65 | −14 | −2 | −7 |
| 3895 | 1 | HR | 80 | +12 | +12 | +32 | +4 | +20 |
|  |  | MBP | 133 | −5 | −9 | −14 | −11 | −13 |
| 3896 | 1 | HR | 76 | 0 | +20 | +36 | +40 | +48 |
|  |  | MBP | 154 | −34 | −38 | −70 | −40 | −23 |
| 3898 | 3 | HR | 96 | +8 | +16 | +48 | +44 | +28 |
|  |  | MBP | 140 | −23 | −31 | −28 | −30 | −16 |
| 3902 | 3 | HR | 104 | −5 | +8 | +3 | −2 | −5 |
|  |  | MBP | 134 | −19 | −33 | −39 | −25 | −8 |
| 3916 | 1 | HR | 92 | +4 | +7 | +13 | +11 | +5 |
|  |  | MBP | 153 | −14 | −32 | −26 | −1 | −5 |
| 3925 | 1 | HR | 108 | +20 | +76 | +44 | +44 | +36 |
|  |  | MBP | 136 | −13 | +10 | −1 | +6 | +2 |
| 3934 | 1 | HR | 80 | −12 | −4 | −12 | −4 | −8 |
|  |  | MBP | 152 | +8 | −3 | −3 | +1 | +4 |
| 3967 | 1 | HR | 124 | −8 | −8 | −4 | −20 | −8 |
|  |  | MBP | 133 | +10 | +1 | +16 | +1 | +7 |
|  |  | HR | 112 | −12 | −12 | +4 | +4 | −4 |
| 3979 | 1 | MBP | 145 | −44 | −29 | −18 | −18 | −23 |
|  |  | HR | 101 | +24 | +28 | +12 | +24 | +28 |
| 3988 | 1 | MBP | 139 | +1 | +13 | +9 | +21 | +16 |
|  |  | HR | 88 | +4 | +20 | +48 | +36 | +28 |
| 3983 | 3 | MBP | 139 | −1 | −1 | −7 | −2 | −8 |
|  |  | HR | 97 | −1 | −5 | −4 | −5 | +3 |
| Hydralazine | 3 | MBP | 111 | −33 | −30 | −40 | −30 | −15 |
|  |  | HR | 103 | +42 | +77 | +86 | +85 | +86 |
| 3902* | 3 | MBP | 143 | −24 | −11 | −20 | −16 | −8 |
|  |  | HR | 92 | +5 | +7 | +20 | +20 | +23 |

*A second batch of this compound was prepared and tested in the dog for confirmatory purposes.

Several prior art benzoquinolizines which were found to be active in the rat test were tested in a single dog to determine if they had the ability to reduce blood pressure without causing tachycardia. The results of these test for compounds having the general formula:

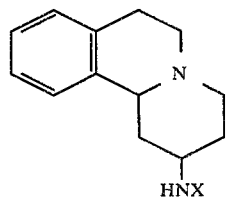

are set out in Table III:

TABLE III
Antihypertensive and Heart Rate Effects of Prior Art Benzoquinolizines in the Dog. Test Dose: 10 mg/kg, p.o.

| TR | X | Parameter | Initial Value | 1 hr | 2 hr | 4 hr | 6 hr | 8 hr |
|---|---|---|---|---|---|---|---|---|
| 2354 | 2,3-dichlorophenyl | MBP, mmHg | 159 | +6 | 0 | −5 | −1 | 0 |
|  |  | HR, b/min | 112 | −8 | −4 | −4 | +12 | +12 |
| 2420 | 2,6-dimethoxy-4-methylphenyl | MBP | 132 | −37 | −17 | +11 | +1 | −6 |
|  |  | HR | 92 | −8 | +20 | +48 | +56 | +24 |
| 2425 | 4-methylphenyl | MBP | 150 | −8 | +1 | −1 | +4 | 0 |
|  |  | HR | 112 | −8 | +12 | +44 | +48 | +40 |
| 2577 | 4-methoxyphenyl | MBP | 113 | +4 | −9 | +5 | +39 | +36 |
|  |  | HR | 124 | +36 | +44 | +48 | 44 | 36 |
| 2783* | benzoyl | MBP | 139 | −6 | −1 | 0 | −2 | 4 |
|  |  | HR | 100 | −3 | +13 | +1 | −1 | +4 |
| 3273 | 4-hydroxyphenyl | MBP | 119 | −19 | −8 | +9 | +15 | +5 |
|  |  | HR | 99 | +41 | +44 | +29 | +10 | +4 |

*Mean values for 3 dogs

From Table III it can be determined that prior art benzoquinolizines found to be active in the rat cannot be expected to be active in the dog test, i.e., possess the ability to lower blood pressure without causing tachycardia. This is especially significant in relation to TR-2873 due to the close structural similarity between this compound and those of the present invention.

Administration of the compounds of the present invention by conventional means produces a lowering of blood pressure in hypertensive individuals. Certain of the compounds relieve hypertension without causing an increase in heart rate. The term "individual" means a human being or an experimental animal that is a model for a human being. The effective dose may vary from individual to individual, but it is readily determined by one skilled in the art without undue experimentation. Medications prepared with the compounds of the present invention as active ingredients are readily formulated by mixing the compounds in dosage units with fillers, carriers, extenders and/or excipients generally used in preparing pharmaceutical formulations. When mixed in such a formulation, the compound may be in the form of a free base but is preferably in the form of a pharmacologically acceptable non-toxic acid addition salt. The medication may be either solid or liquid form and may be compounded as tablets, powders, capsules, suspensions and similar dosage forms according to accepted manufacturing methods. These medications may be administered, for example, orally or subcutaneously, in conformity with recognized pharmacological techniques.

What is claimed is:

1. A trans-2-amido-hexahydrobenzo[a]quinolizine represented by the formula:

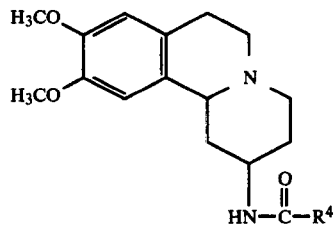

wherein $R^4$ is

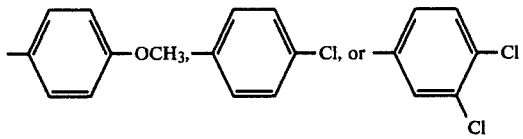

or a pharmaceutically acceptable, non-toxic, acid addition salt thereof.

2. A compound as described in claim 1 wherein $R^4$ is

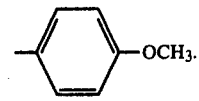

3. A compound as defined in claim 1 wherein $R^4$ is

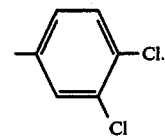

4. A compound as defined in claim 1 wherein $R^4$ is

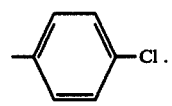

5. 1,3,4,6,7,11b-hexahydro-9,10-dimethoxy-2(4-methoxybenzoylamino)-2H-benzo[a]quinolizine hydrochloride.

6. 2-(3,4-dichlorobenzoylamino)-1,3,4,6,7,11b-hexahydro-9,10-dimethoxy-2H-benzo[a]quinolizine hydrochloride.

7. 2-(4-chlorobenzoylamino)-9,10-dimethoxy-1,3,4,6,7,11b-hexahydro-2H-benzo[a]quinolizine hydrochloride.

* * * * *